(12) United States Patent
Colston et al.

(10) Patent No.: US 6,905,885 B2
(45) Date of Patent: Jun. 14, 2005

(54) PORTABLE PATHOGEN DETECTION SYSTEM

(75) Inventors: Billy W. Colston, Livermore, CA (US); Matthew Everett, Livermore, CA (US); Fred P. Milanovich, Lafayette, CA (US); Steve B. Brown, Livermore, CA (US); Kodumudi Vendateswaran, Livermore, CA (US); Jonathan N. Simon, San Leandro, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/880,515

(22) Filed: Jun. 12, 2001

(65) Prior Publication Data

US 2003/0003441 A1 Jan. 2, 2003

(51) Int. Cl.[7] .................. G01N 33/543; G01N 33/53
(52) U.S. Cl. .................. 436/518; 436/528; 435/7.1; 435/7.92; 435/7.94
(58) Field of Search .................. 435/4, 7.1, 7.92–7.95, 435/174, 287.1, 287.2, 287.7, 970, 971, 973; 436/518, 524, 528, 536, 538, 541, 177, 810, 805, 823, 824

(56) References Cited

U.S. PATENT DOCUMENTS

| 4,952,520 | A | * | 8/1990 | Okusa et al. ............... 436/533 |
| 5,236,826 | A | * | 8/1993 | Marshall .................... 435/7.92 |
| 5,821,066 | A | * | 10/1998 | Pyle et al. .................. 435/7.2 |
| 5,922,617 | A | * | 7/1999 | Wang et al. ................. 436/518 |
| 6,045,996 | A | | 4/2000 | Cronin et al. .................. 435/6 |
| 6,057,107 | A | | 5/2000 | Fulton ......................... 251/11 |
| 6,319,676 | B1 | * | 11/2001 | Nazareth et al. ............. 435/7.5 |
| 6,387,707 | B1 | * | 5/2002 | Seul et al. .................. 436/164 |

OTHER PUBLICATIONS

Fodor et al, Light–directed spatially addressable parallel chemical synthesis, Science, 251, 1991, p–767–773.

* cited by examiner

Primary Examiner—Padmashri Ponnaluri
Assistant Examiner—My-Chau T Tran
(74) Attorney, Agent, or Firm—Eddie E. Scott; L. E. Carnahan; Alan H. Thompson

(57) ABSTRACT

A portable pathogen detection system that accomplishes on-site multiplex detection of targets in biological samples. The system includes: microbead specific reagents, incubation/mixing chambers, a disposable microbead capture substrate, and an optical measurement and decoding arrangement. The basis of this system is a highly flexible Liquid Array that utilizes optically encoded microbeads as the templates for biological assays. Target biological samples are optically labeled and captured on the microbeads, which are in turn captured on an ordered array or disordered array disposable capture substrate and then optically read.

22 Claims, 6 Drawing Sheets

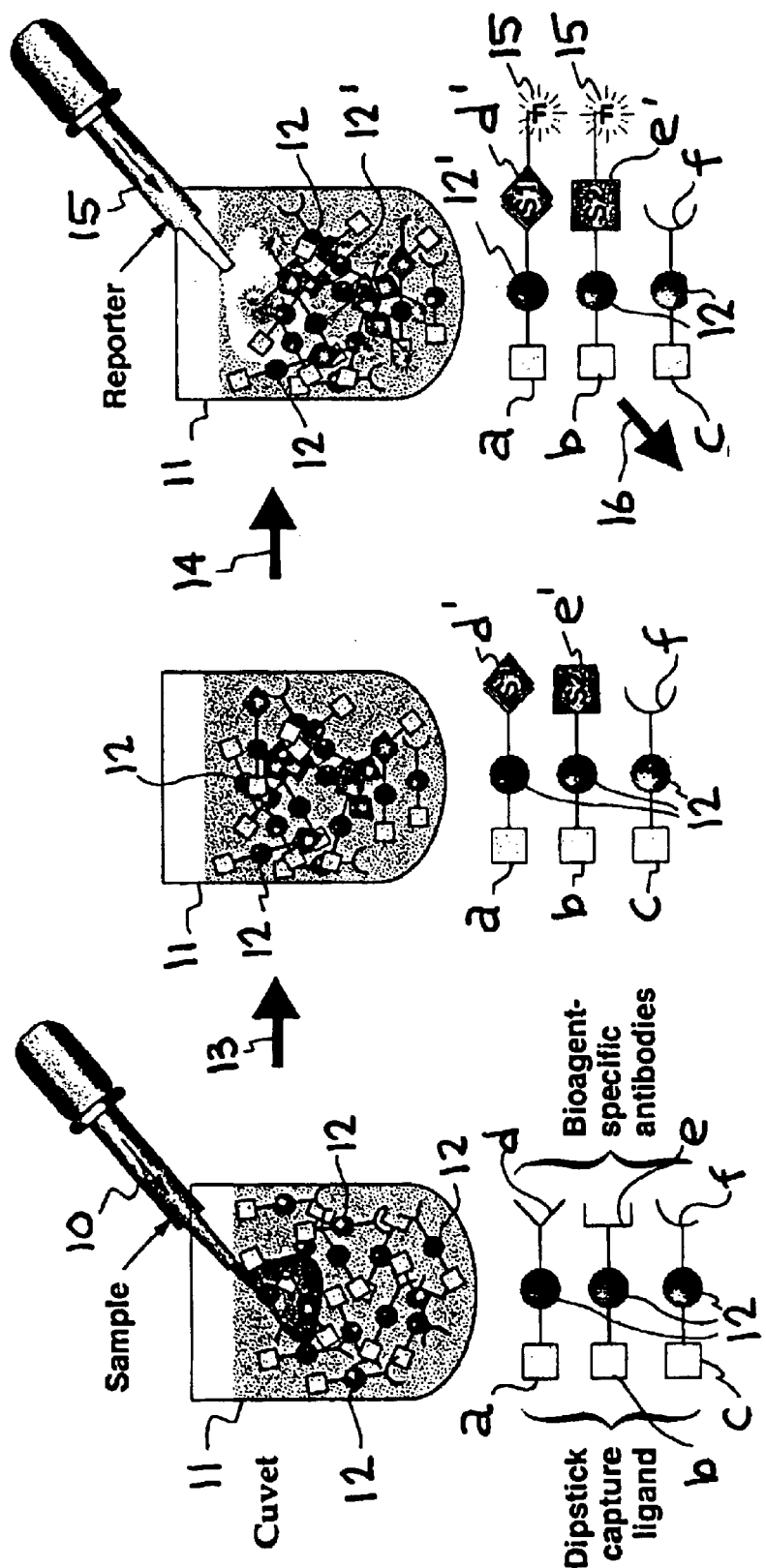

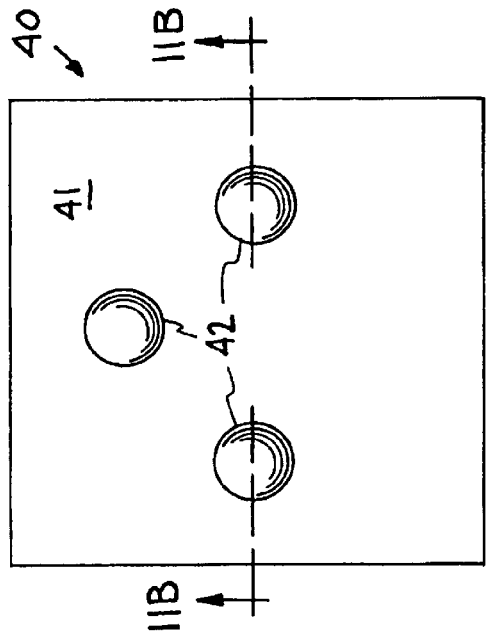
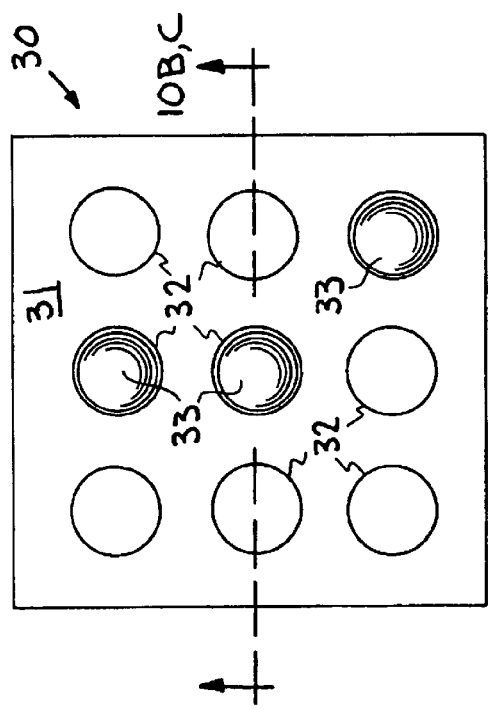
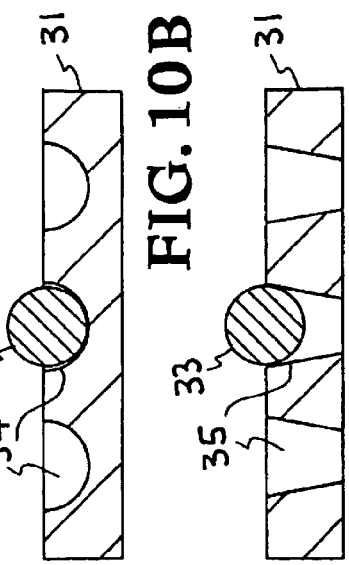
FIG. 11A
FIG. 11B
FIG. 10A
FIG. 10B
FIG 10C

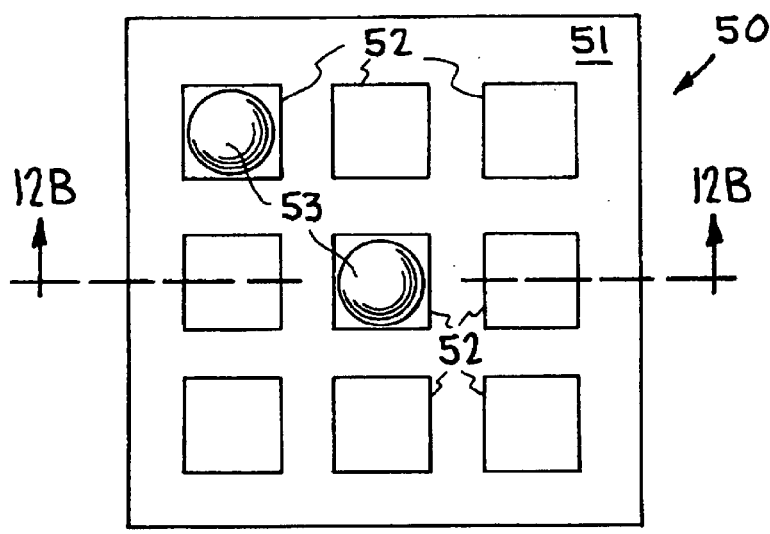
FIG. 12A
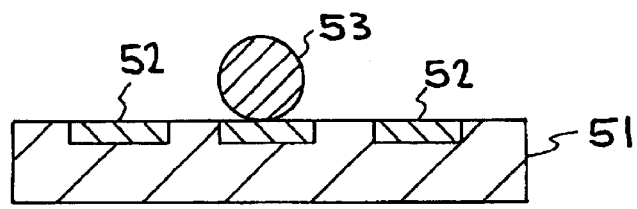
FIG. 12B
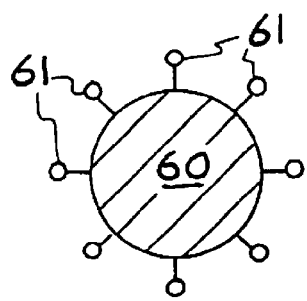 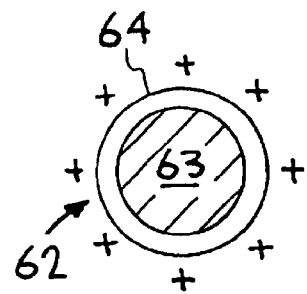 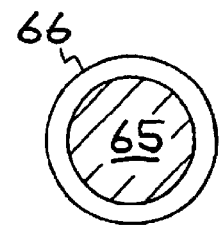
FIG.13A  FIG 13B  FIG 13C

PORTABLE PATHOGEN DETECTION SYSTEM

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to the detection of pathogens and toxins, particularly to a highly flexible liquid array that utilizes optically encoded microbeads as the templates for biological assays, and more particularly to a microimmunoassay (handheld) system wherein target biological samples are optically labeled and captured on microbeads, which are in turn captured on an ordered array or disposable capture substrate and optically read.

The most commonly employed portable pathogen detection is strip-type tests, such as those used in handheld glucose diagnostics or the Joint Biological Point Detection System (JBPDS), a system used for detection of biowarfare agents. These tests are held or 'smart ticket' assay, and are currently the smallest embodiment of a viable pathogen detection technology. In the JBPDS, for example, a membrane strip is printed with three lines: a mobile line of colored latex particles coated with an antibody to the bioagent being detected, a fixed line of a second antibody to the same bioagent, and a fixed line of antibody directed to the antibody on blue latex particles. To perform an assay, a liquid sample is added to the device that hydrates the latex spheres (which are located in the sample well). If the targeted bioagent is present, a complex is formed between the latex sphere and bioagent. This complex wicks through the strip and is captured by the fixed line of antibody to the bioagent forming a visible line of color. A line will also appear at the next fixed line due to capture of free latex spheres. Thus a negative assay will only have a single line at the control line and a positive assay will have two lines.

The JBPDS obtains multiplex capability by delivering multiple "tickets" (printed membrane strips) to the assay by means of a mechanical carousel. Currently, nine different "tickets", each sensitive to a different bioagent, share the sample and perform the analysis with fluidic automation and photonic inspection of the test lines. This technology represents a credible solution for military use since the number of target pathogens is limited. For civilian use, however, the scaling of the device to 30 or more pathogens is quite problematic. The carousel becomes increasingly complicated and large, while dividing the sample between the different assays creates an unacceptable reduction in sensitivity.

The 'DNA Chip' on the other hand, is an emerging technology based on nucleic acid identification of pathogens that has a proven multiplex capability. The chip has its origin in the publication "Light-directed spatially addressable parallel chemical synthesis," Fodor et al, (1991) Science, 251, p. 767–773. Here a format was proposed that allowed for a very dense packing of chemical probe compounds on a silicon substrate. Affymetrix Corp., Santa Clara, Calif. is developing the most promising version of this technology, see U.S. Pat. No. 6,045,996 issued Apr. 4, 2000 to Cronin et. al. By combining solid phase chemical synthesis with modern photolithographic fabrication techniques, Affymetrix Corp. has been able to assemble an array of 65,000 individual and unique nucleic acid probes in an area of several square centimeters. Each probe region consists of thousands of identical molecules in an area or 'patch' 50 microns square. This resulting silicon surface can analyze a complex solution for specific DNA fragments by forming hybridization with its nucleic acid component that has been labeled with a fluorescent dye. In the DNA chip's basic application, replicates of the DNA being analyzed are produced, fractionated and flourescently labeled. They are then exposed to the chip and allowed a period of time to find a complementary sequence on the chip. If this occurs hybridization occurs at the sight or patch containing the complementary DNA sequence. This results in a flourescently labeled region that is read by a raster scanning laser beam and suitable collection optics that preserve spatial resolution.

As powerful as the chip technology is, it does have some significant drawbacks. A single chip design from concept to product can cost as much as $400K. In addition, once its design is determined it cannot be altered. The instrumentation to read the chip is very large and optically fragile. There is a lengthy incubation time to allow for the hybridization of the target. In applications such as bioforensics or proteonics, where new information is constantly being made available, one is committed to a series of costly chip developments to keep the analysis current. Finally, individual chips can be reused only a few times, so this technology is impractical for application requiring the analysis of hundred to thousands of samples.

A sensor array for the measurement and identification of multiple analytes in solution has been developed by J. T. McDevitt et al, University of Texas, as published in International Publication No. WO00/04372 on 27 Jan. 2000, based on U.S. application Ser. No. 09/207,248 filed 7 Apr. 1999. This involves a system for rapid characterization of multi-analyte fluids and, in one embodiment, includes a light source, a sensor array, and a detector. The sensor array is formed from a supporting member into which a plurality of cavities may be formed. A series of chemically sensitive particles, beads, or microspheres are positioned within the cavities. The particles may be configured to produce a signal when a receptor coupled to the particle interacts with the analyte. Using patterned recognition techniques, the analytes within a multi-analyte fluid may be characterized.

A multiplex detection system using a Liquid Array is a more flexible and cost-effective format than either the JBPDS or the DNA chips, described above. By use of the Liquid Array, additional assays can be added simply by addition of different color bead sets. Up to 100-plex assay can now be performed using a 10×10 array of microbead sets developed by Luminex Corporation, Austin, Tex. under U.S. Pat. No. 6,057,107 issued May 2, 2000 to J. R. Fulton. Each microbead is individually doped with two fluorescent dyes (orange and red) as indicated in FIG. 1, wherein a liquid array shows the absolute intensity of the two dyes (orange and red) as indicated by legend and arrows and which provides a method to uniquely identify each microbead set.

Given the existing Luminex Corp. bead set, two different types of multiplex analysis can now occur. The first involves multiplexed detection of different biomarkers in the sample, as seen in FIG. 2 wherein each bead color is used to identify a specific bioagent assay. In this approach, a sample is added to a collection of microbeads. Each color or microbeads contains a capture assay that is specific for a given bioagent. Fluorescent labels are then added to identify the presence of each agent on the bound bead.

In the second type of multiplexed analysis, using the bead set, different microbead colors are used to identify the sample rather than the bioagent. Here, all the microbeads are labeled with the same bioagent assay, with each person assigned a different color, see FIG. 3. Since all the samples can be run in a highly parallel fashion, victims potentially exposed to a pathogen could quickly be screened.

Luminex Corp. developed the Liquid Array concept of FIGS. 1–3 to be used in conjunction with a benchtop flow cytometer. Each optically encoded and flourescently labeled microbead is individually counted for the fraction of a second it passes through the detection system, creating the need for a complex fluidics and optoelectronics package. The Luminex Corp. flow cytometer, therefore, is well suited for laboratory analysis but is neither inexpensive nor compact enough to be used in field or chair-side measurements.

The present invention which utilizes the liquid array approach of Luminex Corp., as described above, involves a method for constructing a portable pathogen detection system that accomplished on-site multiple detection of targets in biological samples. In the system of the invention, a highly flexibly Liquid Array utilizes optically encoded microbeads as the templates for biological assays. The system of this invention basically contains microbead specific reagents, incubation/mixing chambers, a microbead capture array substrate, and an optical measurement and decoding system. Target biological samples are optically labeled and captured on the microbeads, which are in turn captured on an ordered array and optically read.

This invention combines the probability of the smart ticket (JBPDS), the scalability of the DNA chips, and flexibility of the Luminex Corp. flex cytometer to create a powerful multiplex detection platform as set forth in Table 1 shown comparison of MIDS to "Chip" and "Liquid Arrays." This invention intentionally moves away from a laboratory type instrument, where extensive training and elaborate biochemical protocols are necessary. The goal was to approach the simplicity and probability of a JBPDS strip test without compromising the flexibility, sensitivity, and multiplicity of the liquid array paradigm. Like the strip test, the entire sample preparation module is intended to be disposable, with microbead imaging and detection performed on a separate reader device. The use of a disposable, in addition to being a good diagnostic business model, eliminates cross sample contamination and greatly simplified the fluidics.

TABLE 1

|  | Chip | Liquid Array | MIDS |
| --- | --- | --- | --- |
| Flexibility | Fixed template | Beads readily exchanged in set | Beads readily exchanged in set |
| Instrument Cost | ~$250K | $30K | $10K |
| Assay Cost | $400K setup plus $200 per assay | $30K set-up plus $1 per multiplex assay | $40K set-up plus $2 per multiplex assay |
| Speed | Hours | Minutes | Minutes |
| Target | Nucleic acid | DNA, toxin, spore, virus, bacteria | DNA, toxin, spore, virus, bacteria |
| Portability | Benchtop | Benchtop | Handheld |
| Robustness | Controlled Environment | Controlled Environment | Field Environment |

SUMMARY OF THE INVENTION

It is an object of the present invention to provide for on-site multiplex detection of targets in biological samples.

A further object of the invention is to provide a detection system that will allow on-site, real time assay of multiple biomarkers.

A further object of the invention is to provide a portable pathogen detection system that can be used in chair-side or field applications to detect and quantify viruses, microbes, enzymes polymerase chain reaction (PCR) products, toxins, nucleic acids, and any other biological species currently detectable with DNA and immunological assays.

Another object of the invention is to provide portable pathogen detection system that accomplishes on-site multiplex detection of targets in biological samples.

Another object of the invention is to provide portable pathogen detection system containing microbead specific reagents, incubation/mixing chambers, microbead capture array substrates, and an optical measurement and decoding system.

Another object of the invention is to provide a portable pathogen detection system based on a highly flexible Liquid Array that utilizes optically encoded microbeads as the templates for biological assays.

Another object of the invention is to provide a portable pathogen detection system wherein target biological samples are optically labeled and captured on microbeads, which are in turn captured on an ordered array, and optically read.

Other objects and advantages of the present invention will become apparent from the following description and accompanying drawings. Basically, the invention comprises a portable pathogen detection system wherein target biological samples are optically labeled and captured on microbeads, which in turn are captured on a disposable microbead capture array and then optically read. The invention provides a method for constructing a portable pathogen detection system that accomplishes on-site multiplex detection of targets in biological samples. The system contains the following basic components: microbead specific reagents, incubation/mixing chambers, disposable microbead capture arrays, and an optical measurement and decoding system. The basis of this invention is a highly flexible Liquid Array that utilizes optically encoded microbeads as the templates for biological assays. The intrinsic microbead signature is used as a code, providing information about either the origin (i.e. patent ID) or nature of the sample. The extrinsic fluorescence, in the form of a fluoro-immunoassay, is used to provide quantitative information about the targeted biological sample.

This technology will allow on-site, real time assay of multiple biomarkers. It can be used in chairside or field applications to detect and quantify viruses, microbes, enzymes, polymerase chain reaction (PCR) products, toxins, nucleic acids, and any other biological species currently detectable with DNA and immunological assays. Given the current suite and variety of potential threat agents, the flexible and highly parallel nature of this technology makes it particularly well suited for biowarfare agent detection. This platform would provide the capability, for example, to provide on-site screening of virtually any bioagent to soldiers or other potential biowarfare agent victims.

Commercial uses of this technology are likely to focus mainly on biomedical screening and diagnostic applications, although clear applications in bioforensics, drug discovery, and poteomics exist. This art, for example, could be used either as a bedside or field portable unit to rapidly screen and diagnose trauma victims. Alternatively, this technology could be used to track and measure the spread of infectious diseases. A handheld version of this device would be invaluable to emergency response and field biologists for making rapid, on-site determinations that can currently be processed only through a central laboratory. Any biological assay (enzyme, nucleic acid, protein, etc.) usable in a Liquid Array format that reply on point of contact determinations would benefit from this art.

BRIEF DESCRIPTION OF THE DRAWINGS

The accompanying drawings, which are incorporated into and form a part of the disclosure, illustrate the method and an embodiment of the invention and, together with the description, serve to explain the principles of the invention.

FIGS. 4–6 and 7A–7C illustrate the operational sequence of the portable pathogen detection system in accordance with the present invention.

FIG. 10A illustrates a method for physically capturing microbeads on a top view of a disposable capture array surface, which may include either wells or channels.

FIG. 10B is a side view of the FIG. 10A capture array taken along the dashed line B–C of FIG. 10A and wherein capture wells are utilized.

FIG. 10C is a view similar to FIG. 10B but wherein the capture array of FIG. 10A utilized capture channels.

FIGS. 11A and 11B illustrate respective top and side views of a disordered array for the physical capture of microbeads using a microbead capture filter.

FIGS. 12A and 12B illustrate top and side views of a disposable electronic/magnetic capture array for microbeads.

FIGS. 13A, 13B and 13C illustrate enlarged views of microbead configurations, involving optically encoded microbeads, charged microbeads, and microbeads with optically encoded shells.

DETAILED DESCRIPTION OF THE INVENTION

The present invention involves a method an apparatus for on-site multiplex detection of targets in biological samples. More specifically, the invention is directed to a pathogen detection system which incorporates a highly flexible Liquid Array that utilizes optically encoded microbeads as templates for biological assays. The system of the invention includes the following components: microbead specific reagents, incubation/mixing chambers, a microbead capture array, and an optical measurement and decoding system. Target biological samples, such as proteins, ligands, antibodies, and toxins are optically labeled and captured on the microbeads, which are in turn captured and optically read. The intrinsic microbead signature is used as a code, providing information about either the origin (i.e. patent ID) or nature of the sample. The extrinsic fluorescence, in the form of a fluoroimmunoassay, is used to provide quantitative information about the targeted biological sample.

Figure 1:
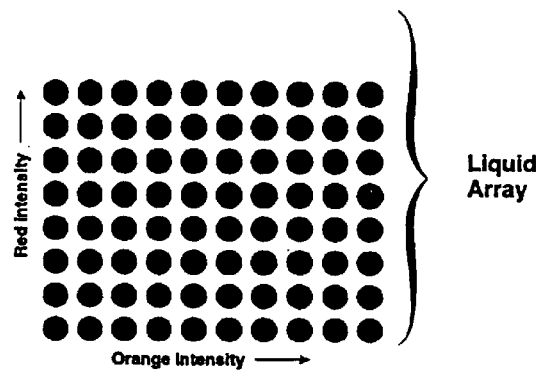
FIG. 1 illustrates a prior art liquid array having orange and red colored dyes of increasing intensity.
Figure 2:
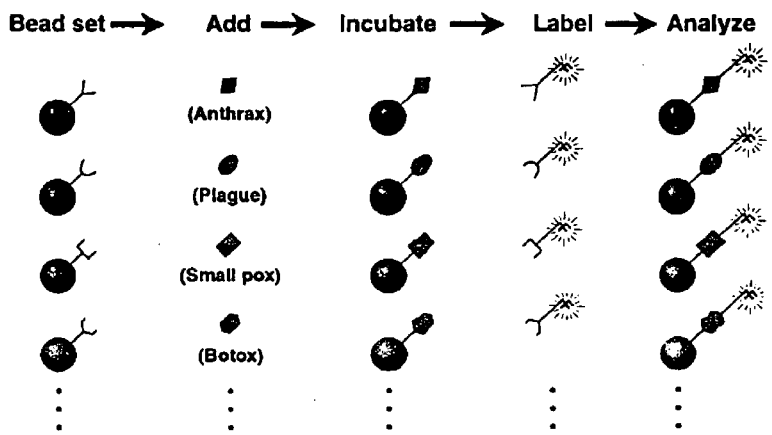
FIG. 2 illustrates a prior art approach wherein each bead color is used to identify a specific bioagent assay.
Figure 3:
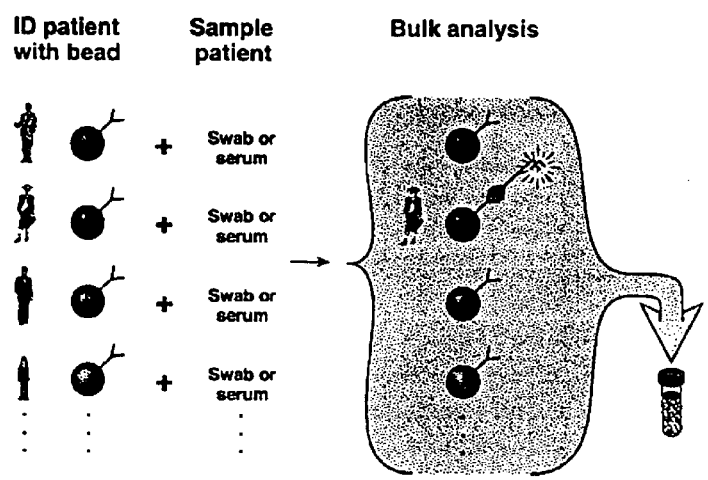
FIG. 3 illustrates a prior art approach wherein each bead color is used to identify an individual rather than a given bioagent, as in FIG. 2.
Figures 7A, 7B, 7C:
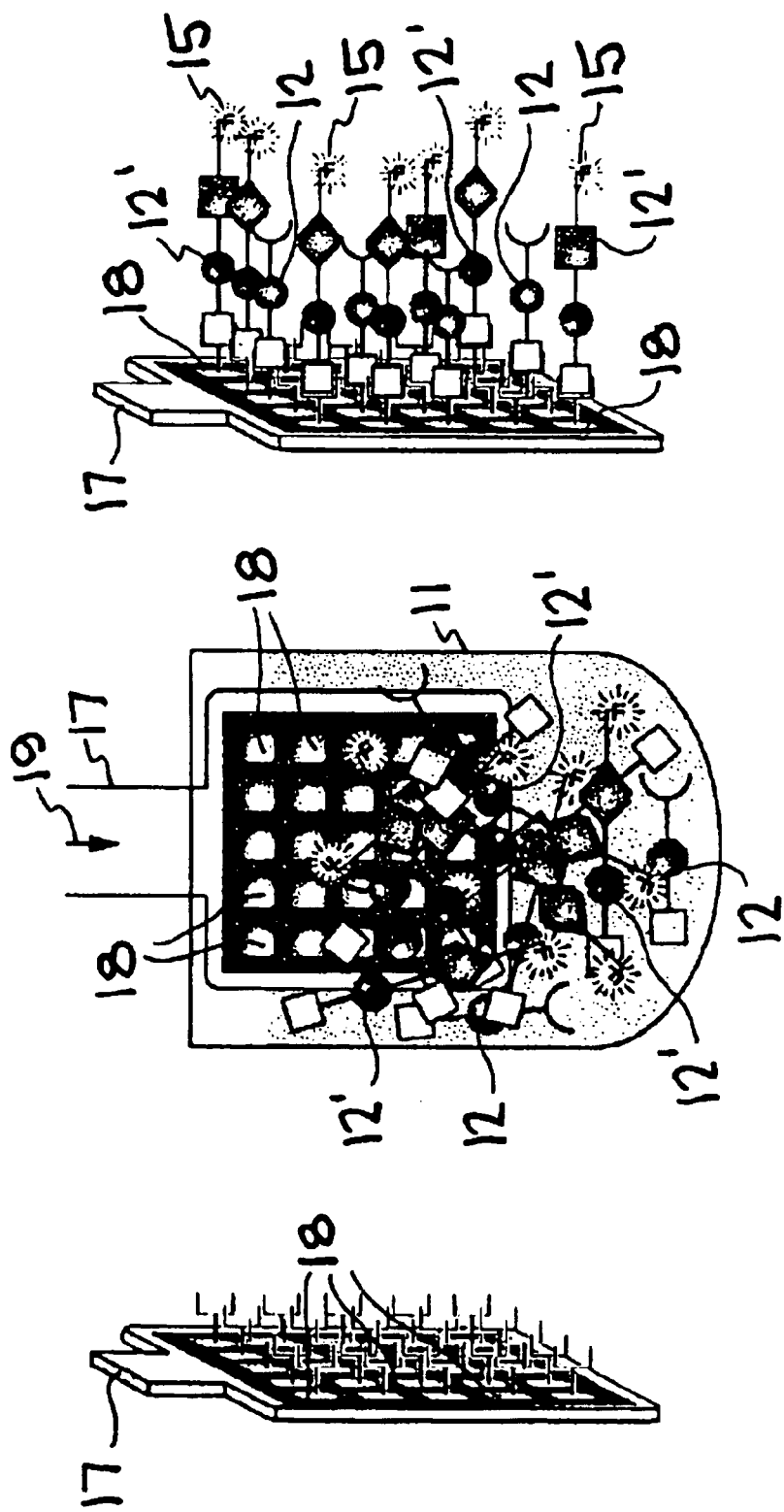

The process of the portable pathogen detection system is illustrated in FIGS. 4–6 and 7A–7C. Sample 10 is added to a cuvet 11 containing optically encoded microbeads 12. Each microbead 12 contains a capture ligand a, b, and c and bioagent-specific antibodies d, e, and f. Each microbead, in addition to the standard sample capture assay, contains special attachment sites. The cuvet 11 is then placed in a mixing holder as indicated by arrow 13 and as shown in FIG. 5 (see FIGS. 8 and 9), providing time for the targeted biological sample to adequately bind the microbeads, as indicated at d' and e'. Then, as indicated by arrow 14, fluorescent reporter labeled antibodies 15 are added to cuvet 11, see FIG. 6, that attach to the microbead bound sample $12^1$. Then, as indicated by arrow 16, a disposable capture substrate 17 containing a patterned array of attachment sites 18, see FIG. 7B, is inserted as indicated by arrow 19, see FIG. 7A, into the cuvet 11. Each attachment site 18 of the array on the disposable capture substrate 17, as seen in FIG. 7B, is designed to capture a single bead 12 or $12^1$, with the spatial distance between each site 18 determined by the resolution of the optical detections systems. After the microbeads 12 and $12^1$ are attached to the sites 18 of substrate 17, as shown in FIG. 7C, the substrate 17 is removed from cuvet 11 located in the mixing holder and placed in a wash receptacle. This wash step improves the sensitivity of the detection process by removing from the disposable capture substrate surface all unbound biological constituents and reducing the background solution florescence. Finally, the disposable microbead capture array is placed in a detection shot or reaction chamber, see FIGS. 8 and 9, where the microbeads are optically decoded for proper identification and measurement of target biological molecules.

Figure 8:
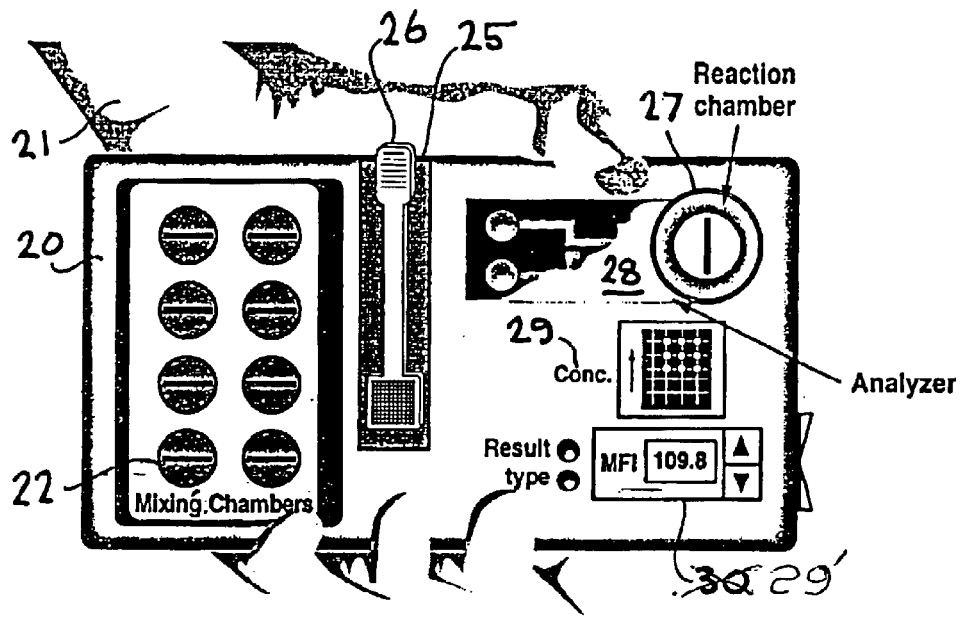
FIG. 8 illustrates a top view of an embodiment of the handheld detection device, with sections removed to illustrate the interior thereof.
Figure 9:
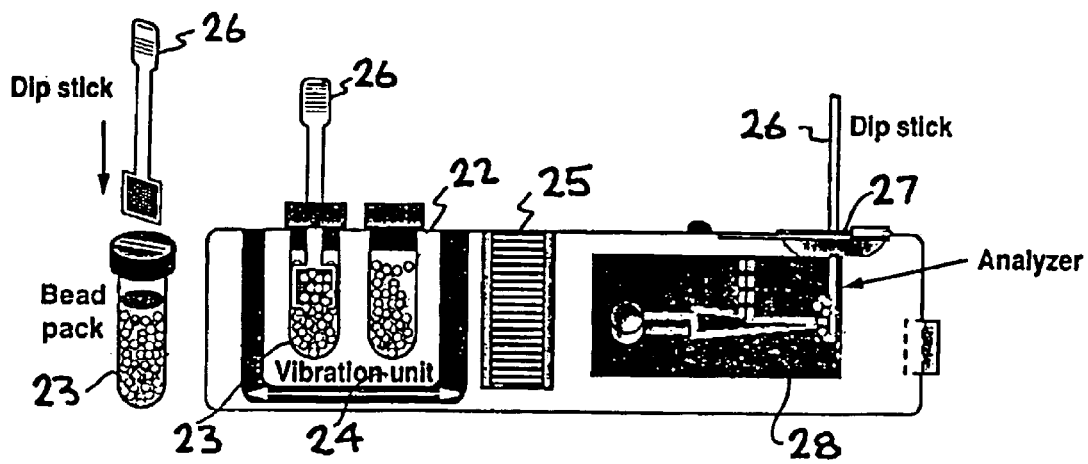
FIG. 9 is a side cross-sectional view of the device of FIG. 8, with a separated bead pack and microbead capture array to more clearly illustrate the operation prior to insertion of the microbead capture array into the vibration unit of the device.

The principal components of the portable pathogen detection system as illustrated in the embodiment of FIGS. 8 and 9, are: 1) optically encoded microbead reagents (bead pack), 2) mixing chambers located in a vibration unit, 3) disposable substrate with ordered microbead attachment array, and 4) optical analyzers each principal component being described in detail below. As shown, the portable pathogen detection system of FIGS. 8 and 9 is a handheld device and comprises a casing or housing 20 which can be held in a human hand 21, the housing 20 including a plurality of mixing chambers 22 within which bead packs 23, see FIG. 9, are located within a vibration or mixing unit 24, an opening 25 within which is located one or more disposable capture substrates 26 for storage purposes prior to insertion thereof into a bead pack 23, see FIG. 9, a reaction chamber 27 into which a disposable capture substrate 26 is finally positioned for at least washing thereof, see FIG. 9, and an analyzer generally indicated at 28 having indicators generally indicated at 29 and 29' on the face of housing 20. The above mentioned four (4) principle components are further described as follows:

FIGS. 10A–10C illustrate the physical capture of microbeads in an ordered array wherein the microbead capture substrate may include an array of wells (FIG. 10B) or an array of channels (FIG. 10C). As shown, the microbead capture array generally indicated at 30 includes a substrate 31 having a plurality of openings 32 therein in which microbeads 33 are captured. The openings 32 of FIG. 10A may constitute a series of wells 34 (FIG. 10B) or a series of channels 35 (FIG. 10C).

FIGS. 11A and 11B illustrate the physical capture of microbeads in a disordered array, wherein the microbead capture array generally indicated at 40 includes a microbead capture filter 41 within which are captured microbeads 42.

Note that there is no order to the captured microbeads by the capture filter 41.

FIGS. 12A and 12B illustrate electronic/magnetic capture of microbeads wherein a capture array generally indicated at 50 includes a substrate 51 having thereon an array of magnetic or electrode capture pads 52 which capture microbeads 53.

FIGS. 13A–13B illustrate embodiments of enlarged microbeads constructed for use with the electronic/magnetic microbead capture array of FIG. 12A–12B. FIG. 13A illustrates an optically encoded microbead 60 having magnetic nano-particles 61 therearound. In FIG. 13B an electrically charged microbead 62 includes a core 63 with an electrically conductive layer or shell 64 thereabout. In FIG. 13C, a magnetic microbead 65 is provided with an optically encoded shell 66.

1) Optically Encoded Microbead Reagents:

Microbead reagents are expected to contain particular sets of target-specific microbeads, allowing highly multiplex detection from a single sample volume. Each microbead in the reagent pack will contain a fluorescent, target-specific assay and an optional capture site for chemically capturing the microbead on the disposable capture substrate. The target can consist of viruses, microbes, enzymes, polymearase chain reaction (PCR) products, toxins, nucleic acids, proteins, and any other Liquid Array detectable biological species.

2) Mixing Chamber:

The mixing chamber imparts kinetic energy to the microbead reagent solution, enchancing binding of the bead-attached assays, target bioagents, and solution phase assays. Since this is essentially a diffusion limited process, maintaining a homogeneous distribution of beads, bioagents, and assays ensures statistically predictable interaction patterns. The mixing chamber platform should be inexpensive, scaleable, and robust. Mixing can be accomplished using thermal, magnetic (stir bars, etc.), electrical (dielectric forces, etc.), acoustical (ultrasound, etc.) or physical processes. It is possible that active mixing, however, is unnecessary, making this component of the portable pathogen detection system optional.

3) Disposable Capture Substrate with Microbead Attachment Array:

Each disposable capture substrate will have an array of microbead attachment sites as shown in FIGS. 7B and 7C. A single microbead will bind to each site, with each site spatially distinct from its neighbors. This configuration should minimize cross-talk and allow single bead optical detection. In addition, the sites should be spatially ordered, simplifying the detection process (i.e., the location of each microbead is known). The array will be set up as a non-selective interface capable of capturing any spatial combination of the optically encoded microbead sets. In a second embodiment of this invention, the microbeads could be captured in a disordered array, where no special effort is made to spatially isolate the microbeads. The burden will reside on the optical analyzer to decode and interpret the captured microbead array.

The microbeads can be attached to the disposable capture substrate by a variety of methods, including magnetic, physical, electrical, and chemical processes. Physical capture could occur by using a flat, filter type material where beads are trapped on the surface. If an ordered array is desirable, this "filter" could contain holes or wells appropriately spaced to allow ordered capture sites for the microbeads. Alternatively, each bead could itself be magnetic or be, labeled with magnetic particles that are captured by a disposable, magnetically activated capture substrate. Electrical capture of the beads could be achieved by creating an array of electrodes on the surface of the capture substrate that attract the partially charged microbeads. Finally, some type of coating could be used on the disposable capture substrate attachment sites to chemically bind the microbeads.

4) Optoelectronics for Optical Assay Detection and Decoding:

The fixed matrix method (i.e., detection of microbeads caught on the disposable capture array) has two major advantages over the Liquid Array approach used by Luminex. The ability to integrate the returned fluorescent signal over longer periods makes inexpensive and compact light sources (LEDs) and detectors (photodiodes) feasible, and detection of the microbead array can occur serially, making incorporation of additional light sources at different wavelengths much easier, thus improving the multiplexing capability of the system.

The optical system consists of the following components: an illustration source, detection electronics, analysis package, and user interface. The simplest types of light sources include light emitting diodes (LEDs), laser, laser diodes, and filament lamps. These sources can be used in conjunction with optical filters, diffraction gratings, prisms, and other optical components to provide a specified spectral component of light. Alternative forms of radiation such as bioluminescence, phosphorescence, and others could also potentially be employed. Although typical fluorphores, require excitation wavelengths in the visible portion of the spectrum (300–700 nm wavelength), other wavelengths in the infrared and ultraviolet portion of the spectrum could also prove useful for illuminating the disposable microbead capture array. The transmitted, reflected, or re-emitted light from the trapped microbeads must then be propagated to an optical apparatus for detection, using photosensitive detectors such as photodiodes or photomultiplier tubes, in combination with some type of spectral and/or spatial filtering. Spatial filtering of the light is possible by either transverse scanning of the disposable capture array or with two-dimensional detectors such as charge coupling device cameras (CCDs) and video cameras.

It has thus been shown that the present invention provides a method and apparatus, using a disposable liquid array approach in a portable pathogen detection system that accomplishes on-site multiplex detection of targets in biological samples. The portable pathogen detection system uses a highly flexible Liquid Array, similar to that used in the Luminex cytometer, and its compact enough to be used as a handheld instrument for field or chair-side measurements. Thus, this approach combines the portability of the JBPDS smart ticket, the scalability of the DNA chip, and flexibility of the Luminex flow cytometer to create a powerful multiplex detection platform, as illustrated above in Table 1.

While particular embodiments of the invention and operational procedures for carrying out the method have been described and or illustrated to exemplify and teach the principles of the invention, such are not intended to be limiting. Modifications and changes may become apparent to those skilled in the art, and it is intended that the invention be limited only the scope of the appended claims.

What is claimed is:

1. A method for detection and measurement of a targeted biological sample, comprising the steps of:
   providing a multiplicity of optically encoded microbeads,
   providing said optically encoded microbeads with a capture ligand,
   providing said optically encoded microbeads with bioagent-specific antibodies,
   placing said optically encoded microbeads into a container,
   adding a sample to said contained optically encoded microbeads, said sample possibly containing the targeted biological sample,
   placing said contained optically encoded microbeads and said sample in a mixing holder for sufficient time for the targeted biological sample to adequately bind said optically encoded microbeads,
   adding fluorescent labeled antibodies to said contained optically encoded microbeads and said sample for attachment to said bioagent-specific antibodies,
   attaching at least some of said optically encoded microbeads to a disposable capture substrate containing an array of individual attachment sites for attaching said optically encoded microbeads thereto wherein each individual attachment site captures a single optically encoded micro bead with capture ligand, bioagent-specific antibody, fluorescent labeled antibody, and any targeted biological sample.
   washing said substrate and attached optically encoded microbeads,
   inserting said substrate into an optical detection system, and
   optically decoding said optically encoded microbeads by identifying said optically encoded microbeads and said fluorescent labeled antibodies for detection and measurement of the targeted biological sample.

2. The method of claim 1, wherein said step of containing said microbeads is carried out by placing said optically encoded microbeads in a cuvet.

3. The method of claim 1, additionally including the step of vibrating said mixing holder during said time said contained optically encoded microbeads are placed therein.

4. The method of claim 1 additionally including the step of designing each of said array of attachment sites on a dipstick to capture a single optically encoded microbead.

5. The method of claim 1, additionally including the step of locating said patterned array of attachment sites on said substrate at a spatial distance between each said array as determined by a resolution of said optical detection system.

6. The method of claim 1, wherein said step of washing said substrate is carried out to improve the sensitivity of the detection process by removing from the substrate surface all unbound biological constituents and reducing the background solution fluorescence.

7. The method of claim 1, including the step of placing said optically encoded microbeads in a disposable bead pack.

8. The method of claim 1, additionally including the steps of providing each said optically encoded microbead with a different color and providing each said optically encoded microbead with a substrate capture point.

9. The method of claim 1, additionally including the step of providing said contained optically encoded microbeads from the group consisting of optically encoded optically encoded microbeads, charged optically encoded microbeads, and optically encoded microbeads with optically encoded shells.

10. The method of claim 1, wherein said step of attaching said optically encoded microbeads is carried out in an ordered array.

11. The method of claim 1, wherein wherein said step of attaching said optically encoded microbeads is carried out in a disordered array.

12. The method of claim 1, wherein said step of attaching said optically encoded microbeads to a disposable capture substrate is carried out by providing said substrate with a plurality of wells or an array of channels.

13. The method of claim 1, wherein said step of attaching said optically encoded microbeads is carried out by an array of magnetic or electrode capture pads.

14. A method for detection and measurement of biological molecules, comprising the steps of:
   providing a quantity of optically encoded microbeads,
   adding a capture ligand to said optically encoded microbeads,
   adding bioagent-specific antibodies to said optically encoded microbeads,
   placing said optically encoded microbeads into a container,
   adding a sample to said contained optically encoded microbeads, said sample possibly containing the biological molecules,
   adding fluorescent labeled antibodies for attachment to said bioagent specific antibodies,
   providing a disposable capture substrate containing an array of individual attachment sites for attaching said optically encoded microbeads thereto,
   inserting said disposable capture substrate containing an array of individual attachment sites into said contained optically encoded microbeads for capturing said optically encoded microbeads wherein each individual attachment site captures a single optically encoded micro bead with capture ligand, bioagent-specific antibody, fluorescent labeled antibody, and any targeted biological molecule,
   washing said substrate and said optically encoded microbeads,
   inserting said disposable capture substrate into a detection system, and
   optically decoding said optically encoded microbeads by identifying said optically encoded microbeads and said fluorescent labeled antibodies for identification and measurement of the biological molecules attached to said optically encoded microbeads.

15. The method of claim 14, additionally including the step of forming said contained optically encoded microbeads to be optically encoded.

16. The method of claim 15, wherein said step of decoding of said optically encoded microbeads is carried out in an optical detecting system.

17. A method for pathogen detection comprising the following steps in any order:
   providing a multiplicity of optically encoded microbeads,
   providing capture ligands that attach to each of said microbeads,
   providing bioagent-specific antibodies that attach to each of said microbeads,
   adding a sample to mix with said microbeads, capture ligands, and bioagent-specific antibodies, said sample containing target biological molecules and bind the microbeads, adding fluorescent labeled antibodies to mix with said microbeads, capture ligands, bioagent-specific antibodies, and target biological molecules, for attachment to said target biological molecules, inserting a disposable capture substrate containing an array of individual attachment sites into said microbeads, capture ligands, bioagent-specific antibodies, and target biological molecules for capturing said microbeads, each individual attachment site capturing a single micro bead with capture ligand, bioagent-specific antibody, fluorescent labeled antibody, and any target biological molecule, and optically decoding said microbeads using an optical detection system for optically decoding said microbeads for identification and measurement the said target biological molecules.

18. The method of claim 17, wherein said microbeads are placed in a mixing holder for sufficient time for said target biological molecules to adequately bind with said bioagent-specific antibodies.

19. The method of claim 17, wherein said placing said microbeads in a mixing holder is carried out prior to adding said fluorescent labeled antibodies.

20. The method of claim 17, additionally including washing said disposable capture substrate and said microbeads.

21. The method of claim 17, wherein said array of attachment sites define a patterned array.

22. The method of claim 17, wherein said array of attachments sites define an ordered array.

* * * * *